United States Patent

Assmann et al.

Patent Number: 5,792,873
Date of Patent: Aug. 11, 1998

[54] SUBSTITUTED (1,4) DIOXINO (2,3-F) BENZOIMIDAZOLE DERIVATIVES AND THEIR USE IN PEST CONTROL

[75] Inventors: Lutz Assmann, Eutin; Albrecht Marhold, Leverkusen; Heinz-Wilhelm Dehne, Bonn; Gerd Hänssler, Leverkusen; Klaus Stenzel, Düsseldorf; Ulrike Wachendorff-Neumann, Neuwied, all of Germany

[73] Assignee: Bayer Aktiengesellschaft, Leverkusen, Germany

[21] Appl. No.: 818,651

[22] Filed: Mar. 19, 1997

Related U.S. Application Data

[62] Division of Ser. No. 737,075, Oct. 29, 1996, Pat. No. 5,648,316.

[30] Foreign Application Priority Data

May 3, 1994 [DE] Germany ............ 44 15 435.6

[51] Int. Cl.$^6$ .............................. C07D 491/056
[52] U.S. Cl. ............................ 548/302.1
[58] Field of Search ...................... 548/302.1

[56] References Cited

U.S. PATENT DOCUMENTS

| | | | |
|---|---|---|---|
| 5,310,747 | 5/1994 | Enomoto et al. | 514/395 |
| 5,510,364 | 4/1996 | Lunkenheimer et al. | 514/395 |

FOREIGN PATENT DOCUMENTS

| | | |
|---|---|---|
| 517476 | 12/1992 | European Pat. Off. |
| 545204 | 6/1993 | European Pat. Off. |
| 630570 | 12/1994 | European Pat. Off. |
| 4237567 | 5/1994 | Germany |

Primary Examiner—José G. Dees
Assistant Examiner—Laura L. Stockton
Attorney, Agent, or Firm—Sprung Kramer Schaefer & Briscoe

[57] ABSTRACT

Described herein are new benzimidazole derivatives of the formula

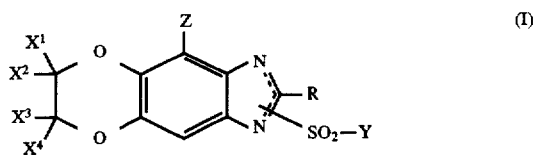

in which
R represents cyano or the group

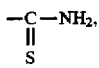

$X^1$, $X^2$, $X^3$ and $X^4$ are identical or different and represent halogen;

Y represents alkyl, alkenyl or alkinyl, each of which is optionally substituted by halogen; or represents optionally substituted phenylalkyl or in each case optionally substituted cycloalkyl and cycloalkenyl; and Z represents hydrogen or halogen, a process for the preparation of these substances, and their use for controlling pests.

New intermediates and processes for their preparation.

2 Claims, No Drawings

SUBSTITUTED (1,4) DIOXINO (2,3-F) BENZOIMIDAZOLE DERIVATIVES AND THEIR USE IN PEST CONTROL

This application is a divisional of application Ser. No. 08/737,075, filed Oct. 29, 1996, now U.S. Pat. No. 5,648,316 which is a 371 of PCT/EP95/01500 filed Apr. 20, 1995.

The invention relates to new benzimidazole derivatives, to a process for their preparation, and to their use as pesticides. The invention furthermore also relates to new intermediates and processes for their preparation.

It has been disclosed that certain benzimidazole derivatives such as, for example, 2-cyano-3-dimethylaminosulfonyl-6,6,7,7-tetrafluoro-[1,4]dioxino[2,3,-f]benzimidazole or 2-cyano-6,6-difluoro-2-dimethylaminosulfonyl-[1,3]dioxolo[4,5-f]benzimidazole, have fungicidal, or fungicidal and acaricidal, properties (cf. EP-A 0 517 476 and DE-OS (German Published Specification) 4 139 950). However, the efficacy of these prior-art compounds is not entirely satisfactory in all sorts of application, in particular when low rates are applied.

There have now been found new benzimidazole derivatives of the formula

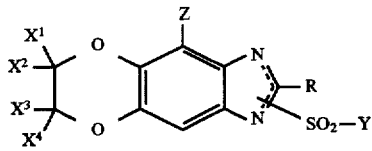

(I)

where

R represents cyano or the group

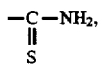

$X^1$, $X^2$, $X^3$ and $X^4$ are identical or different and represent halogen;

Y represents alkyl, alkenyl or alkinyl, each of which is optionally substituted by halogen; or represents optionally substituted phenylalkyl, or in each case optionally substituted cycloalkyl and cycloalkenyl; and Z represents hydrogen or halogen.

Depending on the nature of the substituents, the compounds of the formula (I) can exist as geometrical and/or optical isomers or variously composed isomer mixtures. The invention relates to the pure isomers and to the isomer mixtures.

In formula (I), the broken line represents a double bond between one of the two nitrogen atoms and the adjacent carbon atom which has attached to it the substituent R. The nitrogen atom which does not participate in the double bond has attached to it in each case the —SO$_2$—Y radical.

Furthermore, it has been found that benzimidazole derivatives of the formula (I) are obtained when benzimidazoles of the formula

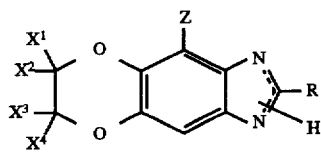

(II)

where

R, $X^1$, $X^2$, $X^3$, $X^4$ and Z have the abovementioned meaning are reacted with sulphonyl chlorides of the formula Cl—SO$_2$—Y    (III)

in which

Y has the abovementioned meaning, if appropriate in the presence of a diluent and if appropriate in the presence of a reaction auxiliary.

Furthermore, it has been found that benzimidazole derivatives of the formula (I) are highly suitable for use as pesticides. They are distinguished, in particular, by a potent fungicidal, insecticidal and acaricidal activity.

Surprisingly, the benzimidazole derivatives according to the invention display a better activity than the prior-art compounds of the most similar constitution.

Formula (I) provides general definition of the compounds according to the invention.

R preferably represents cyano or the group

$X^1$, $X^2$, $X^3$ and $X^4$ are identical or different and preferably represent fluorine, chlorine or bromine.

Y preferably represents $C_1$–$C_6$-alkyl, $C_2$–$C_6$-alkenyl and $C_2$–$C_6$-alkinyl, each of which is optionally monosubstituted to pentasubstituted by identical or different halogen substituents; or represents phenyl-$C_1$–$C_4$-alkyl which can be monosubstituted to trisubstituted in the phenyl moiety by identical or different substituents from the series consisting of halogen, $C_1$–$C_4$-alkyl, $C_1$–$C_4$-halogenoalkyl having 1 to 5 identical or different halogen atoms, $C_1$–$C_4$-alkoxy and/or $C_1$–$C_4$-halogenoalkoxy having 1 to 5 identical or different halogen atoms, or represents $C_3$–$C_7$-cycloalkyl which can be monosubstituted to trisubstituted by identical or different substituents from the series consisting of halogen, $C_1$–$C_4$-alkyl and/or $C_1$–$C_4$-halogenoalkyl having 1 to 5 identical or different halogen atoms, or represents $C_5$–$C_7$-cycloalkenyl which can be monosubstituted to trisubstituted by identical or different substituents from the series consisting of halogen, $C_1$–$C_4$-alkyl and/or $C_1$–$C_4$-halogenoalkyl having 1 to 5 identical or different halogen atoms.

Z preferably represents halogen, fluorine, chlorine or bromine.

R particularly preferably also represents cyano or the group of the formula

$X^1$, $X^2$, $X^3$ and $X^4$ are identical or different and particularly preferably represent fluorine, chlorine or bromine.

Y particularly preferably represents $C_1$–$C_4$-alkyl, $C_2$–$C_4$-alkenyl and $C_2$–$C_4$-alkinyl, each of which is optionally monosubstituted to pentasubstituted by identical or different fluorine and/or chlorine substituents; or represents phenyl-$C_1$–$C_2$-alkyl which can be monosubstituted to trisubstituted in the phenyl moiety by identical or different substituents from the series consisting of fluorine, chlorine, bromine, $C_1$–$C_4$-alkyl, $C_1$–$C_2$-alkoxy, $C_1$–$C_2$-halogenoalkyl having 1 to 5 fluorine and/or chlorine atoms and $C_1$–$C_2$-halogenoalkoxy having 1 to 5 fluorine and/or chlorine atoms, or represents $C_3$–$C_7$-cycloalkyl which can be monosubstituted to trisubstituted by identical or different substituents from the series consisting of fluorine, chlorine, bromine, $C_1$–$C_4$-alkyl and/or $C_1$–$C_2$-halogenoalkyl having 1 to 5 fluorine and/or chlorine atoms, or represents $C_5$–$C_7$-cycloalkenyl which can be monosubstituted to trisubstituted by identical or different substituents from the series consisting of fluorine, chlorine, bromine, $C_1$–$C_4$-alkyl and/or $C_1$–$C_2$-halogenoalkyl having 1 to 5 fluorine and/or chlorine atoms.

Z particularly preferably represents halogen, fluorine, chlorine or bromine.

R very particularly preferably also represents cyano or the group of the formula

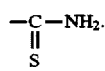

$X^1$, $X^2$, $X^3$ and $X^4$ are identical or different and very particularly preferably represent fluorine, chlorine or bromine.

Y very particularly preferably represents methyl, ethyl, n- or i-propyl, n-, i-, s- or t-butyl, allyl, n- or s-butenyl; propargyl, n- or s-butinyl; methyl, ethyl, allyl, n- or s-butenyl, propargyl and n- or s-butinyl, each of which is monosubstituted to trisubstituted by identical or different fluorine and/or chlorine substituents; or represents benzyl or phenethyl, it being possible for each of these radicals to be monosubstituted to trisubstituted in the phenyl moiety by identical or different substituents from the series consisting of fluorine, chlorine, bromine, methyl, ethyl, methoxy, trifluoromethyl and/or trifluoromethoxy, or represents cyclopropyl, cyclopentyl, cyclohexyl, cyclopentenyl and cyclohexenyl, it being possible for each of these radicals to be monosubstituted to trisubstituted by identical or different substituents from the series consisting of fluorine, chlorine, bromine, methyl, n- or i-propyl, chloromethyl, dichloromethyl and/or trifluoromethyl.

Z very particularly preferably represents hydrogen, fluorine or chlorine.

As far as this is possible, the hydrocarbon radicals mentioned above in the definition of the compounds according to the invention, such as alkyl, are in each case straight-chain or branched, also in connection with other atoms, such as halogenoalkyl.

Examples of the compounds according to the invention are listed in Tables 1 to 6.

TABLE 1

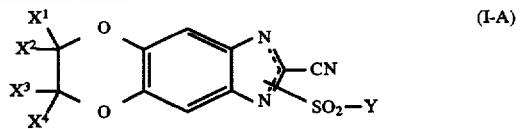 (I-A)

| Compound No. | Y |
|---|---|
| 1 | –$C_2H_5$ |
| 2 | –$C_3H_7$-i |
| 3 | 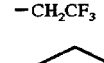 |

-continued

| Compound No. | Y |
|---|---|
| 4 | –$C_3H_7$-n |
| 5 | –$C_4H_9$-n |
| 6 | –$CH(CH_3)C_2H_5$ |
| 7 | –$CF_3$ |
| 8 | –$CH_2CF_3$ |
| 9 | 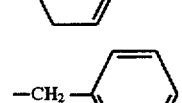 |
| 10 | –$CH_2$– 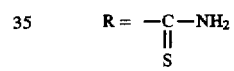 |

Table 2

Table 2 contains compounds of the formula (I) in which R=CN, $X^1$=F, $X^2$=F, $X^3$=Cl, $X^4$=F and Y has the meanings tabulated in Table 1.

Table 3

Table 3 contains compounds of the formula (I) in which R=CN, $X^1$=F, $X^2$=Cl, $X^3$=Cl, $X^4$=F and Y has the meanings tabulated in Table 1.

Tables 4 to 6

Tables 4 to 6 contain those compounds of the formula (I) in which $$R = -\underset{\underset{S}{\parallel}}{C} - NH_2$$

and $X^1$, $X^2$, $X^3$ $X^4$ and Y have the meanings tabulated in Tables 1 to 3.

If, for example, 2-cyano-6,6,7,7-tetrafluoro-[1,4]dioxino[2,3-f]benzimidazole and methanesulphonyl chloride are used as starting materials, the course of the reaction of the process according to the invention can be represented by the following equation:

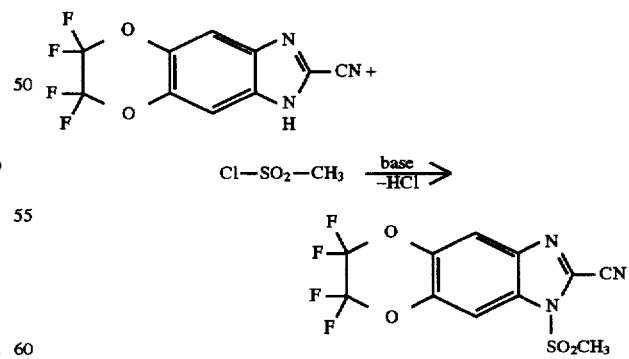

Formula (II) provides a general definition of the benzimidazoles required as starting materials for carrying out the process according to the invention. In formula (II), R, $X^1$, $X^2$, $X^3$, $X^4$ and Z preferably, or particularly preferably, have those meanings which have already been mentioned above in connection with the description of the compounds of the formula (I) as being preferred, or particularly preferred, for R, $X^1$, $X^2$, $X^3$, $X^4$, R and Z.

Some of the benzimidazoles of the formula (II) have been disclosed (cf. EP-A 0 517 476 or DE-OS (German Published Specification) 4 139 950). They can be prepared by reacting phenylenediamines of the formula (IV)

[structure: phenylenediamine with $X^1$, $X^2$, $X^3$, $X^4$, Z, two O, two $NH_2$]

in which $X^1$, $X^2$, $X^3$, $X^4$ and Z have the abovementioned meanings with methyl 2,2,2-trichloroacetimidate, of the formula $$Cl_3C-\underset{\underset{NH}{\|}}{C}-OCH_3,\qquad (V)$$

in the presence of glacial acetic acid at temperatures between 10° C. and 40° C. and reacting the resulting 2-trichloromethyl-benzimidazoles of the formula (VI)

[structure: benzimidazole with $X^1$, $X^2$, $X^3$, $X^4$, Z, $C(Cl)_3$, H]

in which $X^1$, $X^2$, $X^3$, $X^4$ and Z have the abovementioned meanings with aqueous ammonia solution in the presence of a diluent, such as, for example, ethanol, at temperatures between 0° C. and 40° C., and, if appropriate, reacting the resulting benzimidazoles of the formula (II-A)

[structure: benzimidazole with $X^1$, $X^2$, $X^3$, $X^4$, Z, CN, H]

in which $X^1$, $X_2$, $X_3$, $X_4$ and Z have the abovementioned meanings with hydrogen disulphide in the presence of a diluent, such as, for example, ethanol, at temperatures between 10° C. and 100° C., if appropriate in the presence of an acid-binding agent, such as, for example, triethylamine.

The compounds of the formulae (VI-1)

[structure: Cl, F, Cl, F substituted dioxino-benzimidazole with $CCl_3$]

and (II-1)

[structure: Cl, F, Cl, F substituted dioxino-benzimidazole with CN]

and (II-2)

[structure: Cl, F, Cl, F substituted dioxino-benzimidazole with $C(=S)-NH_2$]

are new. They can be prepared following the above process by reacting 6,7-diamnino- 2,3-dichloro-2,3-difluoro-[1,4]-benzodioxane, of the formula (IV-1)

[structure: Cl, F, Cl, F substituted benzodioxane with two $NH_2$]

with methyl 2,2,2-trichloroacetimidate, of the formula $$Cl_3C-\underset{\underset{NH}{\|}}{C}-OCH_3,\qquad (V)$$

in the presence of glacial acetic acid at temperatures between 10° C. and 40° C., reacting the resulting 6,7-dichloro-6,7-difluoro-2-trichloromethyl-[1,4]-dioxino-[2,3-f]-benzimidazole, of the formula (VI-1)

[structure: Cl, F, Cl, F substituted dioxino-benzimidazole with $CCl_3$]

with aqueous ammonia solution in the presence of a diluent, such as, for example, ethanol, at temperatures between 0° C. and 40° C., and, if appropriate, reacting the resulting 2-cyano-6,7-dichloro-6,7-difluoro-[1,4]-dioxino-[2,3-f]-benzimidazole, of the formula (II-1)

[structure: Cl, F, Cl, F substituted dioxino-benzimidazole with CN]

with hydrogen disulphide in the presence of a diluent, such as, for example, ethanol, at temperatures between 10° C. and 100° C., if appropriate in the presence of an acid-binding agent, such as, for example, triethylamine.

Some of the phenylenediamines of the formula (IV) have been disclosed (cf. EP-A 0 517 476, DE-OS (German Published Specification) 4 139 950, DE-OS (German Published Specification) 3 621 301 and DE-OS (German Published Specification) 3 605 977) They can be prepared by reacting 1,4-benzodioxanes of the formula.

(VII)

[structure: benzene ring with $X^1$, $X^2$, $X^3$, $X^4$, Z, two O]

in which $X^1$, $X_2$, $X_3$, $X_4$ and Z have the abovementioned meanings with a mixture of nitric acid and sulphuric acid (which may also comprise oleum) at temperatures between 0° C. and 100° C. and either reducing the resulting dinitro-1,4-benzodioxanes of the formula

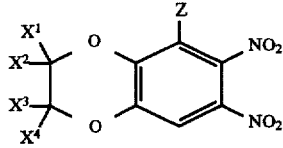

(VIII)

in which

X$^1$, X$_2$, X$_3$, X$_4$ and Z have the abovementioned meanings at temperatures between 50° C. and 100° C., for example using iron in the presence of aqueous hydrochloric acid and ethanol, or reacting them catalytically with elemental hydrogen at temperatures between 25° C. and 100° C. and under a pressure of between 1 and 100 bar and in the presence of metals or metal compounds of sub-group VIII of the Periodic System of Table Elements, in particular nickel or palladium, as catalysts (cf also the preparation examples).

6,7-Diamino-2,3-dichloro-2,3-difluoro-[1,4]-benzodioxane, of the formula

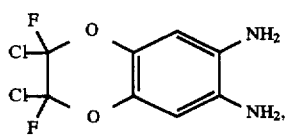

(IV-1)

was hitherto unknown. It can be prepared from the above process, either by reducing 2,3-dichloro-2,3-difluoro-6,7-dinitro[1,4]-benzodioxane, of the formula

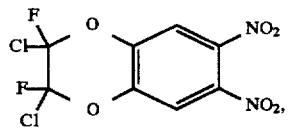

(VIII-1)

at temperatures between 50° C. and 100° C., for example using iron in the presence of aqueous hydrochloric acid and ethanol, or reacting them catalytically with elemental hydrogen at temperatures between 25° C. and 100° C. and under a pressure of between 1 and 100 bar and in the presence of metals or metal compounds of sub-group VIII of the Periodic Table of the Elements, in particular nickel or palladium, as catalysts (cf. also the preparation examples).

2,3-Dichloro-2,3-difluoro-6,7-dinitro-[1,4]-benzodioxane, of the formula

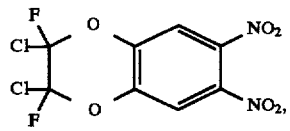

(VIII-1)

was also hitherto unknown. The compound of the formula (VIII-1) can be prepared by reacting 2,3-dichloro-2,3-difluoro-[1,4]-benzodioxane, of the formula

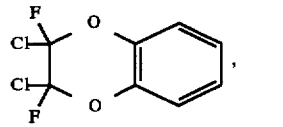

(VII-1)

with a mixture of nitric acid and sulphuric acid, if appropriate in the presence of oleum, at temperatures between 0° C. and 100° C.

2,3-Dichloro-2,3-difluoro-[1,4]-benzodioxane, of the formula (VII-1), was hitherto unknown. The compound can be prepared by reacting 2,2,3,3-tetrachloro-[1,4]-benzodioxane, of the formula

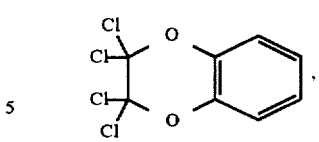

(VII-2)

with anhydrous hydrofluoric acid in an autoclave at temperatures between −10° C. and +70° C. (cf. preparation examples).

Diluents which are suitable for carrying out the process according to the invention are inert organic solvents. The following can preferably be used: aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran, ethylene glycol dimethyl ether or ethylene glycol diethyl ether, ketones such as acetone or butanone or methyl isobutyl ketone; nitriles such as acetonitrile, propionitrile or benzonitrile, or esters such as methyl acetate or ethyl acetate.

The process according to the invention is preferably carried out in the presence of a suitable reaction auxiliary. Suitable reaction auxiliaries are all customary inorganic or organic bases. The following can preferably be used: alkaline earth metal hydroxides or alkali metal hydroxides, such as sodium hydroxide, calcium hydroxide, potassium hydroxide or else ammonium hydroxide, alkali metal carbonates, such as sodium carbonate, potassium carbonate, potassium hydrogen carbonate, sodium hydrogen carbonate, alkali metal acetates or alkaline earth metal acetates, such as sodium acetate, potassium acetate or calcium acetate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between 0° C. and 150° C., preferably at temperatures between 20° C. and 120° C.

The process according to the invention is normally carried out under atmospheric pressure. However, it is also possible to carry out the process under elevated or reduced pressure.

To carry out the process according to the invention, 1.0 to 2.0 mol, preferably 1.0 to 1.3 mol, of sulphonyl chloride of the formula (III) and, if appropriate, 1.0 to 2.0 mol, preferably 1.0 to 1.3 mol, of reaction auxiliary are generally employed per mole of benzimidazole of the formula (II) in a diluent. The reaction is carried out and the reaction products are worked up and isolated by customary methods (cf. also preparation examples).

The active compounds of the formula (I) according to the invention have a potent action against pests and can be employed in practice for controlling undesirable harmful organisms. The active compounds are suitable for use as crop protection agents, in particular as fungicides.

Fungicidal agents are employed in crop protection for controlling Plasmodiophoromycetes, Oemycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum*;
Phytophthora species, such as, for example, *Pseudoperonospora humuli* or *Pseudoperonospora cubensis*;
Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechlera, syn: Helminthosporium);

Uromyces species, such as, for example, *Uromyces appendiculatus*;

Puccinia species, such as, for example, *Puccinia recondita*;

Tilletia species, such as, for example, *Tilletia caries*;

Ustilago species, such as, for example, *Ustilago nuda* or *Ustilago avenae*;

Pellucularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae*;

Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

In this context, the active compounds according to the invention can be employed particularly successfully for controlling diseases in fruit and vegetable growing, such as, for example, against the pathogen causing tomato blight (*Phytophthora infestans*) or against the pathogen causing apple scab (*Venturia inaequalis*) or against the pathogen causing downy mildew on grapevines (*Plasmopara viticola*) or for controlling rice diseases, such as, for example, against the pathogen causing rice blast disease (*Pyricularia oryzae*).

Moreover, the active compounds according to the invention have a good in-vitro activity.

In addition, the active compounds according to the invention are suitable for controlling animal pests, preferably arthropods and nematodes, particularly insects and arachnida encountered in agriculture, in forests, in the protection of stored products and materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*.

From the order of the Anoplura, for example, *Phylloxera vastatrix, Pemphigus spp., Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp:, Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*.

From the order of the Arachnida, for example, *Scorpio maurus* and *Latrodectus mactans*.

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*.

The plant-parasitic nematodes include *Pratylenchus spp., Radopholus similis, Ditylenchus dipsaci, Tulenchulus semipenetrans, Heterodera spp., Meloidogyne spp., Aphelenchoides spp., Longidorus spp., Xiphinema spp.* and *Trichodorus spp.*, The active compounds of the formula (I) according to the invention are also distinguished by an outstanding acaricidal activity, for example against the greenhouse red spider mite (*Tetranychus urticae*). They also have a good foliar-acting insecticidal activity.

Depending on their particular physical and/or chemical properties, the active compounds can be converted into the customary formulations, such as solutions, emulsions, suspensions, powders, foams, pastes, granules, aerosols, microcapsulations in polymeric substances and in coating compositions for seed, and ULV cold mist and warm mist formulations.

These formulations are produced in a known manner, for example by mixing the active compounds with extenders, that is, liquid solvents, liquefied gases under pressure, and/or solid carriers, optionally with the use of surfactants. If water is used as the extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, alcohols such as butanol or glycol and their ethers and esters, ketones such as acetone, methyl ethyl ketone, methyl iso-butyl ketone or cyclohexanone, strongly polar solvents such as dimethylformamide and dimethyl sulphoxide, and water; liquefied gaseous extenders or carriers are to be understood as meaning liquids which are gaseous at ambient temperature and under atmospheric pressure, for example aerosol propellants such as halogenohydrocarbons and butane, propane, nitrogen and carbon dioxide; suitable solid carriers are: for example ground natural minerals such as kaolins, clays, talc, chalk, quartz, attapulgite, montmorillonite or diatomaceous earth, and ground synthetic minerals such as highly-disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocynaine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

When used as fungicides, the active compounds according to the invention, as such or in their formulations, can also be used as a mixture with known fungicides, bactericides, acaricides, nematicides or insecticides, for example to widen the spectrum of action or to prevent the build-up of resistance. In many cases, synergistic effects are obtained, i.e. the activity of the mixture is higher than the activity of the individual components.

Examples of particularly advantageous components in mixtures are the following compounds:

Fungicides:

2-aminobutane; 2-anilino-4-methyl-6-cyclopropyl-pyrimidine; 2',6'-dibromo-2-methyl-4'-trifluoromethoxy4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran; carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, *nitenpyram*, omethoate, oxamyl, oxydemethon M, oxydeprofos, parathion A, parathion M, permethrin, phenthoate, phorate, phosalone, phosmet, phosphamdon, phoxim, piriniicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators is also possible.

When used as fungicides, the active compounds can be used as such, in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on or the like.

It is furthermore possible to apply the active compounds by the ultra low volume method, or to inject the preparation of active compound, or the active compound itself, into the soil. The seed of plants may also be treated.

In the treatment of potted plants, the active compound concentrations in the use forms can be varied within a substantial range when used as fungicides. They are generally between 1 and 0.0001% by weight, preferably between 0.5 and 0.001%.

When used as fungicides, amounts of active compound of from 0.001 to 50 g, preferably 0.01 to 10 g, are generally required per kilogram of seed in the case of seed treatment.

When used as fungicides, active compound concentrations of from 0.00001 to 0.1% by weight, preferably from 0.0001 to 0.02%, are required at the site of action in the case of soil treatment.

When used as insecticides and acaricides, the active compounds according to the invention, in their commercially available formulations and in the use forms prepared from the formulations, may be present in the form of a mixture with other active compounds such as insecticides, attractants, sterilants, acaricides, nematicides, fungicides, growth regulators or herbicides. The insecticides include, for example, phosphates, carbamates, carboxylates, chlorinated hydrocarbons, phenyl ureas, substances produced by microorganisms, and the like.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambdacyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, Demeton M, demeton-S-methyl, demeton S, Diazinon, Dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, Imidacloprid, Nitenpyram, N-[(6-chloro-3-pyridinyl) methyl]-N'-cyano-N-methyl-ethanimidamide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyd, milbemectin, pymetrozine, tebufenpyrad, triazuron, aldicarb, bendiocarb, benfuracarb, carbofuran, carbosulfan, chloroethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyfoximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

When used as insecticides and acaricides, the active compounds according to the invention can furthermore be present in their commercially available formulations and in the use forms prepared from these formulations in the form of a mixture with synergists. Synergists are compounds by which the activity of the active compounds is increased without it being necessary for the synergist added to be active itself.

When used as insecticides and acaricides, the active compound content of the use forms prepared from the conmmercially available formulations can vary within wide limits. The active compound concentration of the use forms can be from 0.0000001 up to 95% by weight of active compound, preferably between 0.0001 and 1% by weight.

They are applied in the customary manner adapted to suit one of the use forms.

Preparation and use of the active compounds according to the invention can be seen from the examples which follow.

PREPARATION EXAMPLES

EXAMPLE 1

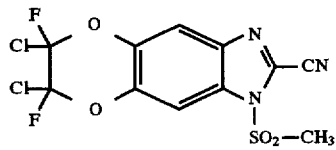
(I-1)

4.6 g (15 mmol) of 2-cyano-6,7-dichloro-6,7-difluoro-[1,4]dioxino[2,3-f]benzimidazole are added in portions with stirring at room temperature to a mixture of 0.6 g (1 5 mmol) of 60% sodium hydride in 70 ml of tetrahydrofuran. Stirring is continued for 30 minutes at room temperature, 4.6 g (30 mmol) of methanesulphonyl chloride are then added, the mixture is refluxed for 12 hours.

After cooling, the solution is poured in 400 ml of water. The mixture is extracted three times using in each case 100 ml of methylene chloride, and, after drying, the combined organic extracts are concentrated under. reduced pressure. The residue obtained is subsequently crystallized by stirring with 20 ml of ether.

This gives 4.9 g (85% of theory) of 2-cyano-6,7-dichloro-6,7-difluoro-3-methylsulphonyl-[1,4]dioxino[2,3-f] benzimidazole of melting point 123° to 126° C.

Preparation of the Starting Materials

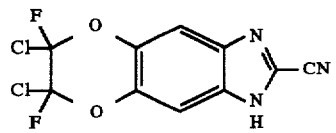
(II-1)

59.7 g (0.15 mol) of 6,7-dichloro-6,7-difluoro-2-trichloromethyl-[1,4]dioxino[2,3-f]benzimidazole are added with stirring at room temperature to a mixture of 250 ml of concentrated aqueous ammonia solution and 200 ml of ethanol.

The mixture is stirred for 20 hours at room temperature and then acidified using hydrochloric acid. The reaction mixture is extracted three times using in each case 150 ml of methylene chloride. The organic extracts are dried and concentrated. The residue obtained is then purified by chromatography and silica gel using diethyl ether as the eluent.

This gives 23.8 g (52% of theory) of 2-cyano-6,7-dichloro-6,7-difluoro-[1,4]dioxino[2,3-f]benzimidazole of melting point >230° C.

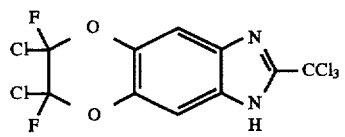
(VI-1)

54.0 g (0.3 mol) of methyl 2,2,2-trichloroacidimidate are added dropwise with stirring at room temperature to a mixture of 54.2 g (0.20 mol) of 6,7-diamino-2,3-dichlbro-2,3-difluoro-[1,4]-benzodioxane and 200 ml of glacial acetic acid. After the addition has ended, stirring is continued for 20 hours at room temperature. 300 ml of water are then added, and the resulting precipitate is filtered off and dried.

This gives 63.1 g (79% of theory) of 6,7-dichloro-6,7-difluoro-2-trichloromethyl-[1,4]dioxino[2,3-f]benzimidazole of melting point >230° C.

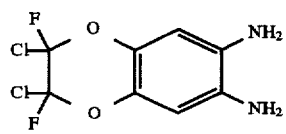
(IV-1)

316 g (0.95 mol) of 2,3-dichloro-2,3-difluoro-6,7-dinitro-[1,4]-benzodioxane in 1500 ml of tetrahydrofuran together with 30 g of Raney nickel are introduced into a hydrogenating autoclave, and the mixture is flushed with hydrogen and subsequently hydrogenated by injecting 30 to 50 bar hydrogen at 25° to 45° C. When no more hydrogen is absorbed, the autoclave is cooled and the pressure is released. The solvent is distilled off after removal of the catalyst by filtration.

This gives 246 g of 6,7-diamino-2,3-dichloro-2,3-difluoro-[1,4]-benzodioxane of melting point 130° to 131° C.

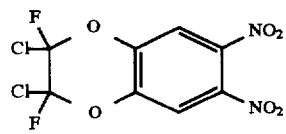
(VIII-1)

400 g of mixed acid (33% by weight of HNO$_3$, 67% by weight of H$_2$SO$_4$) are introduced into a stirred apparatus at 20° C., and 200 g of 2,3-dichloro-2,3-difluoro-1,4-benzodioxane are added dropwise at room temperature with stirring. The mixture is stirred for 1 hour at 20° C. and then for 1 hour at 40° C. 100 ml of 20% oleum are then added dropwise. Stirring is continued for 2 hours at 40° C. and then for 3 hours at 50° C. After the mixture has cooled, it is transferred to 500 g of ice, and the product is taken up in dichloromethane. After washing with water, the solution is dried and subsequently freed from solvent.

This gives 245 g of 2,3-dichloro-2,3-difluoro-6,7-dinitro-[1,4]-benzodioxane

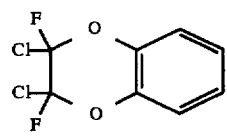
(VII-1)

1800 ml of anhydrous hydrogen fluoride are introduced into a fluorination apparatus, and 1300 g of 2,2,3,3- tetrachloro-[1,4]-benzodioxane are introduced at −10° C. The autoclave is then sealed and the contents heated to 60° C., with stirring. After the evolution of hydrogen chloride has ceased (pressure released by means of a condenser), the mixture is cooled, the hydrogen fluoride is distilled off, and the residue is transferred onto ice. After phase separation, the organic product is dried and distilled.

This gives 665 g of 2,3-dichloro-2,3-difluoro-1,4-benzodioxane of boiling point 82° to 83° C./18 mbar.

Example 2

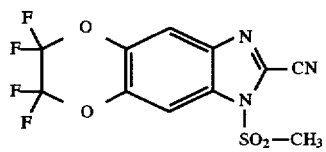
(I-2)

5.4 g (40 mmol) of pulverized potassium carbonate are added, at room temperature, to 5.4 g (20 mmol) of 2-cyano-6,6,7,7-tetrafluoro[1,4]dioxino[2,3-f]benzimidazole in 100 ml of acetonitrile, 4.6 g (30 mmol) of methanesulphonyl chloride are then added dropwise with stirring at room temperature, and, after the addition has ended, the mixture is refluxed for 6 hours. The reaction mixture is subsequently cooled to room temperature and poured into 500 ml of water. The mixture is extracted three times using in each case 150 ml of methylene chloride. The combined organic phases are dried over sodium sulphate and freed from solvent under reduced pressure.

This gives 5.5 g (79% of theory) of 2-cyano-3-methylsulfonyl-6,6,7,7-tetrafluoro[1,4]dioxino[2,3-f]benzimidazole of melting point 180° to 183° C.

The compounds of the formula listed in the table below are prepared analogously to Examples 1 and 2 and following the general description of the process according to the invention.

| Ex. No | $X^1$ | $X^2$ | $X^3$ | $X^4$ | Z | R | Y | m.p. (°C.) |
|---|---|---|---|---|---|---|---|---|
| 3 | F | F | F | F | H | CN | —$C_2H_5$ | 177–84 |
| 4 | F | F | F | F | H | CN | —$CH_2$—⌬ | 153–57 |
| 5 | F | F | F | F | H | CN | —$CH_2$—$C(CH_3)$=$CH_2$ | 90–94 |
| 6 | F | F | F | F | H | CN | —$(CH_2)_3Cl$ | 133–36 |

Use Examples

The use examples which follow, the compounds given below were employed as parison substances.

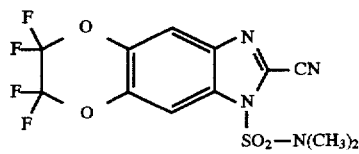

2-cynao-3-dimethylaminosulphonyl-6,6,7,7-tetrafluoro-[1,4]dioxino[2,3-f]benzimidazole

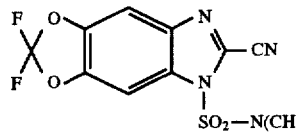

2-cynao-6,6-difluoro-3-dimethylaminosulphonyl-[1,3]dioxolo[4,5-f]benzimidazole

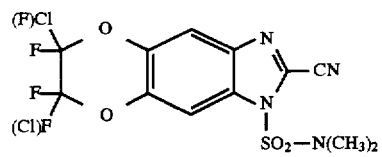

2-cyano-3-dimethylaminosulphonyl-6,6,7-trifluoro-7-chloro (or 6,6,7-trifluoro-6-chloro)-[1,4]-dioxino-[2,3-f]-benzimidazole (All disclosed in EP-A 0 517 476 or DE-OS (German Published Specification) 4 139 950).

Example A

Venturia test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism *Venturia inaequalis* and then remain in an incubation cabin at 20° C. and 100% relative atmospheric humidity for 1 day.

The plants are then placed in a greenhouse at 20° C. and a relative atmospheric humidity of about 70%.

Evaluation takes place 12 days after the inoculation.

In this test, an efficacy of over 80% is shown, at an active compound concentration of 10 ppm, by the compounds of the formulae (I-1) and (1-2), while the comparison substances (A), (B) and (C) have an efficacy of 43%, 0% and 18%, respectively.

TABLE A

Venturia test (apple)/protective

| Active ingredient | | Efficacy in % of the untreated control at an active compound concentration of 10 ppm in the spray mixture |
|---|---|---|
| [Structure: benzimidazole with CF$_2$-O-CF$_2$ dioxole, CN, SO$_2$-N(CH$_3$)$_2$] | (A) (known) | 43 |
| [Structure: benzimidazole with CF$_2$ dioxole, CN, SO$_2$-N(CH$_3$)$_2$] | (B) (known) | 0 |
| known [Structure: benzimidazole with (F)Cl/(Cl)F substituted dioxole, CN, SO$_2$-N(CH$_3$)$_2$] | (C) | 18 |
| according to the invention [Structure: benzimidazole with CF$_2$-O-CF$_2$ dioxole, CN, SO$_2$-CH$_3$] | (I-2) | 99 |
| [Structure: benzimidazole with FCl/ClF dioxole, CN, SO$_2$-CH$_3$] | (I-1) | 84 |

Example B

Pyriculaia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease level is carried out 4 days after the inoculation.

In this test, an efficacy of 90% is shown, as an active compound concentration of 0.025%, by the compound of the formula (I-2), while the comparison substance (A) has an efficacy of 10%.

TABLE B

Pyricularia test (rice)/protective

| Active compound | | Active compound concentration in % | Efficacy in % of the untreated control |
|---|---|---|---|
| 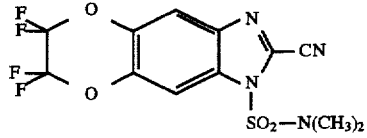 | (A) (known) | 0.025 | 10 |
| 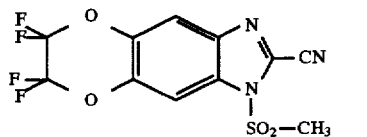 | (I-2) | 0.025 | 90 |

Example C

Tetranychus test (OP resistant/immersion treatment)

Solvent: 7 parts by weight of acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are severely infested with all stages of the greenhouse red spider mite *Tetranychus urticae* are immersed in a preparation of the active compound of the desired concentration.

After the desired periods of time, the activity in % is determined. 100% means that all the spider mites have been killed; 0% means that none of the spider mites have been killed.

In this test, a degree of destruction of over 90% is shown, at an active compound concentration of 0.001% after 13 days, by the compound of the formula (I-2), while the comparison substance (A) causes a degree of destruction of 60%.

TABLE C

Tetranychus test (OP resistant/immersion treatment)

| Active compound | | Active compound concentration in % | Efficacy in % of the untreated control |
|---|---|---|---|
| 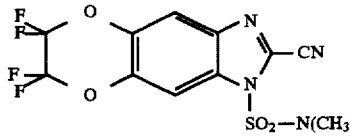 | (A) (known) | 0.001 | 60 |
| 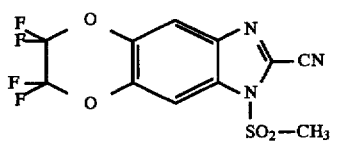 | (I-2) | 0.001 | 98 |

We claim:
1. A compound of the formula:
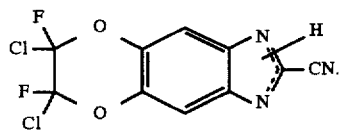
2. A process for preparing a compound according to claim 1, said process comprising reacting 6,7-dichloro-6,7-difluoro-2-trichloromethyl-[1,4]-dioxino-[2,3-f]-benzimidazole, which has the formula:
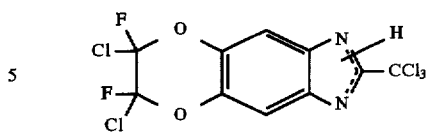
with an aqueous ammonia solution in the presence of a diluent.
* * * * *